US011051516B2

(12) United States Patent
Smyth et al.

(10) Patent No.: US 11,051,516 B2
(45) Date of Patent: Jul. 6, 2021

(54) ANTIMICROBIAL SANITIZER COMPOSITIONS AND THEIR USE

(71) Applicant: GFS CORPORATION AUS PTY LTD, Narangba (AU)

(72) Inventors: Paul Geoffrey Smyth, Murarrie (AU); Michael Paul Bralkowski, Lexington, NC (US)

(73) Assignee: Global Bioprotect IP Pty Ltd, Willoughby (AU)

( * ) Notice: Subject to any disclaimer, the term of this patent is extended or adjusted under 35 U.S.C. 154(b) by 0 days.

(21) Appl. No.: 15/126,855

(22) PCT Filed: Mar. 17, 2015

(86) PCT No.: PCT/AU2015/050111
§ 371 (c)(1),
(2) Date: Sep. 16, 2016

(87) PCT Pub. No.: WO2015/139085
PCT Pub. Date: Sep. 24, 2015

(65) Prior Publication Data
US 2017/0094974 A1    Apr. 6, 2017

(30) Foreign Application Priority Data

Mar. 17, 2014    (AU) ............................... 2014900900

(51) Int. Cl.
| | | |
|---|---|---|
| *A01N 55/00* | (2006.01) | |
| *A01N 47/44* | (2006.01) | |
| *A61K 8/60* | (2006.01) | |
| *A61K 31/695* | (2006.01) | |
| *A61Q 17/00* | (2006.01) | |
| *A61K 8/41* | (2006.01) | |
| *A61K 8/893* | (2006.01) | |
| *A61K 8/39* | (2006.01) | |
| *A61K 8/84* | (2006.01) | |
| *A01N 33/12* | (2006.01) | |

(52) U.S. Cl.
CPC ............ *A01N 55/00* (2013.01); *A01N 33/12* (2013.01); *A01N 47/44* (2013.01); *A61K 8/39* (2013.01); *A61K 8/416* (2013.01); *A61K 8/604* (2013.01); *A61K 8/84* (2013.01); *A61K 8/893* (2013.01); *A61K 31/695* (2013.01); *A61Q 17/005* (2013.01)

(58) Field of Classification Search
None
See application file for complete search history.

(56) References Cited

U.S. PATENT DOCUMENTS

| | | |
|---|---|---|
| 5,686,089 A | 11/1997 | Mitra et al. |
| 5,954,869 A | 9/1999 | Elfersy et al. |
| 6,113,815 A | 9/2000 | Elfersy et al. |
| 6,120,587 A | 9/2000 | Elfersy et al. |
| 6,221,828 B1 | 4/2001 | Matsuo et al. |
| 6,762,172 B1 | 7/2004 | Elfersy et al. |
| 2003/0069317 A1* | 4/2003 | Seitz, Jr. ................ A01N 31/08 514/731 |
| 2003/0073600 A1 | 4/2003 | Avery et al. |
| 2007/0042198 A1 | 2/2007 | Schonemyr et al. |
| 2009/0192231 A1* | 7/2009 | Lemons ................. A01N 37/02 514/738 |
| 2011/0206790 A1 | 8/2011 | Weiss et al. |
| 2013/0053422 A1* | 2/2013 | Edmonds ............. A61K 9/0014 514/372 |
| 2013/0108557 A1* | 5/2013 | Abram ................. A61K 9/0014 424/45 |
| 2014/0011766 A1 | 1/2014 | Krafft |

FOREIGN PATENT DOCUMENTS

| | | |
|---|---|---|
| EP | 1152741 B1 | 10/2006 |
| WO | 2001041567 A1 | 6/2001 |
| WO | 2011002929 A1 | 1/2011 |
| WO | 2012037615 A1 | 3/2012 |
| WO | 2014138821 A1 | 9/2014 |

OTHER PUBLICATIONS

International Search Report in International Application No. PCT/AU2015/050111, dated Jun. 5, 2015, 7 pages.
Sahu, Pankaj et al.: "Therapeutic and Medicinal Uses of Aloe vera: A Review", Pharmacology & Pharmacy, 2013, vol. 4, pp. 599-610.
Extended European Search Report, EP Application No. 15764961.7 (published as EP 3 119 404), dated Nov. 11, 2017 (6 pages).
Third Party Submission dated Feb. 16, 2021, from U.S. Appl. No. 16/867,501.

* cited by examiner

*Primary Examiner* — Robert A Wax
*Assistant Examiner* — Randeep Singh
(74) *Attorney, Agent, or Firm* — Perkins Coie LLP

(57) ABSTRACT

The present invention relates to antimicrobial sanitizing compositions for use as skin sanitizers, especially sanitizers for the hands and feet, and air sanitizers and deodorisers. The sanitizing compositions comprise a combination of three ammonium compounds (ie. an alkoxy silyl ammonium compound, a benzalknonium chloride or benzethonium chloride and a polymeric biguanide) in a non-ionic surfactant carrier. The non-ionic surfactant system comprises an alcohol ethoxylate and an alkylglucoside or alkylpolyglycoside. Methods of use of the compositions are also described.

14 Claims, No Drawings

ANTIMICROBIAL SANITIZER COMPOSITIONS AND THEIR USE

This application is a U.S. National Stage Application of International Application No. PCT/AU2015/050111, filed Mar. 17, 2015, which claims priority to Australian Provisional Application No. 2014900900, filed Mar. 17, 2014, the contents of each of which are hereby incorporated herein by reference in their entireties.

FIELD OF THE INVENTION

The present invention relates to antimicrobial sanitizing compositions for use as skin sanitizers, especially sanitizers for the hands and feet, and air sanitizers and deodorisers. The sanitizing compositions comprise a combination of three ammonium compounds in a non-ionic surfactant carrier. Methods of use of the compositions are also described.

BACKGROUND OF THE INVENTION

Today in the age of advanced medical device technology and antibiotic medicines, the world is faced with hospitals and common facilities such as schools and governmental agencies that have cultured antibiotic resistant microorganisms. The Center for Disease Control (CDC) estimates that more than two million people are affected by antibiotic-resistant infections every year in the United States, with at least 23,000 dying as a result. Hospital nosocomial infections have generated the terms methacillin resistant *Staphylococcus aureus* (MRSA), vancomycin resistant *Enterococcus* (VRE), carbapenem-resistant Enterobacteriaceae (CRE), multi-drug resistant tuberculosis (MRT TB) and *Clostridium difficile* (C Dif) as a listing for infections caused by bacteria which have mutated to become resistant to common antibiotics. While microorganisms are transferred both by contact and aerosol, hand washing and effective hand sanitization are visible means to reduce the spread of microorganisms, especially antibiotic resistant microorganisms.

Effective hand sanitizers are needed as a prophylactic measure for health care workers, patients and visitors to kill common germs on the hand's skin surface in medical facilities. According to Boyce J M, et al in Guideline for Hand Hygiene in Health-Care Settings "Hand hygiene is considered the most important measure for preventing health-care-associated infections and the spread of antimicrobial resistant pathogens."

Health-care workers can also contaminate their hands with *S. aureus*, enterococci, or *Clostridium difficile* by doing clean procedures or touching intact areas of skin of hospitalized patients. Studies have estimated the frequency of health-care workers' glove contamination with MRSA after contact with a colonized patient. Health-care workers were intercepted after a patient-care episode and cultures were taken from their gloved hands before hand washing took place; 17% (95% CI 9-25) of contacts with patients, patient clothing, or patient beds resulted in transmission of MRSA from a patient to the health-care worker's gloves.

Alcohol hand sanitizers are effective on contact but after the alcohol evaporates there is no means to control microbial growth. Gelled alcohol sanitizers using hydroxyethyl cellulose or carbopols trap the dead cells and bacteria on the surface of the skin after the alcohol has evaporated. Alcohol hand sanitizers are also flammable resulting in fires, in skin burns by accident and on purpose as acts of terror. Patient misuse of these products as intoxicants has been reported in prisons, emergency rooms, and medical units.

Furthermore, continued ethanol use in hand sanitisers causes skin damage and this is a problem for health-care workers that need to use alcohol based hand-sanitizers on a regular basis. There is a need for non-alcohol based hand sanitizers that are antimicrobially effective and long lasting.

Advantageously, the present invention provides a sanitizing composition for skin and air that contains no alcohol, is antimicrobially effective on a wide range of microorganisms including Gram negative bacteria, Gram positive bacteria, viruses, fungi and protozoa, and has persistent and/or long lasting activity.

SUMMARY OF THE INVENTION

In a first aspect of the present invention there is provided a sanitizing composition comprising:
  i) an alkoxy silyl ammonium film-forming compound;
  ii) a benzalkonium or benzethonium chloride;
  iii) a polymeric biguanide; and
  iv) a surfactant system comprising:
    a) an alcohol ethoxylate; and
    b) an alkylglucoside or alkylpolyglycoside.

In another aspect of the invention, there is provided a method of sanitizing or disinfecting skin, especially hands or feet comprising applying to the skin of a subject, the hand-sanitizing composition of the present invention.

In a further aspect of the invention, there is provided a method of treating or preventing a fungal infection of the skin, comprising applying the sanitizing composition of the invention to the skin of a subject.

In yet another aspect of the present invention, there is provided a method of deodorising and/or sanitizing the air comprising dispersing the composition according to the invention into the air.

DESCRIPTION OF THE INVENTION

Sanitizing Compositions

In a first aspect of the present invention, there is provided a sanitizing composition comprising:
  i) an alkoxy silyl ammonium film-forming compound;
  ii) a benzalkonium or benzethonium chloride;
  iii) a polymeric biguanide; and
  iv) a surfactant system comprising:
    a. an alcohol ethoxylate; and
    b. an alkylglucoside or alkylpolyglycoside.

In some embodiments, the alkoxy silyl ammonium film-forming agent is an alkoxy silyl quaternary ammonium film forming agent. Alkoxy silyl quaternary ammonium film forming agents are also known in the art as organosilicon quaternary ammonium film forming compounds.

In some embodiments, the alkoxy silyl ammonium film-forming agent is a compound of formula (I):

$$[(R_1O)_3Si\text{-}A\text{-}N^+(W)(X)(Y)]M^- \qquad (I)$$

wherein each $R_1$ is independently selected from hydrogen and —$C_{1-6}$alkyl;
A is a $C_{1-6}$alkylene group;
W and X are independently selected from —$C_{1-6}$alkyl;
Y is a $C_{10-20}$alkyl group; and
M is an anionic counterion.

In particular embodiments, one or more of the following applies:
R₁ is hydrogen, methyl or ethyl, especially methyl or ethyl, more especially methyl;
A is a $C_{2-4}$ alkylene group, especially —CH₂CH₂CH₂—;
W and X are independently selected from methyl and ethyl, especially methyl;
Y is $C_{10-19}$ alkyl; especially $C_{10}$ alkyl or $C_{18}$ alkyl, more especially $C_{18}$ alkyl; and
M is selected from F⁻, Cr⁻, Br⁻ and I⁻, especially Cl⁻.

In particular embodiments, the alkoxy silyl ammonium film-forming compound of formula (I) is selected from 1-octadecanaminium-N,N-dimethyl-N-[3-trimethoxysilyl (propyl)]chloride (also known as 3-trimethoxysilylpropyl-N,N-dimethyl-N-octadecyl ammonium chloride), 3-triethoxysilylpropyl-N,N-dimethyl-N-octadecyl ammonium chloride, 3-triethoxysilylpropyl-N,N-dimethyl-N-isodecyl ammonium chloride and 3-trimethoxysilylpropyl-N,N-dimethyl-N-isodecyl ammonium chloride.

The alkoxy silyl ammonium film-forming compound is present in the composition in an amount in the range of 0.1% to 1.5% w/w, especially about 0.3% to 1.0% w/w, more especially about 0.4 to 0.6% w/w of the composition. It is known that alkoxy silyl quaternary ammonium compounds hydrolyse in water forming the trihydroxy silicon functional group, therefore, for example, 3-trimethoxysilylpropyl-N,N-dimethyl N-octadecyl ammonium chloride is hydrolysed to form as 3-trihydroxysilyl propyl-N,N-dimethyl-N-octadecyl ammonium chloride.

In some embodiments, the benzalkonium or benzethonium chloride compound is a compound of formula (II):

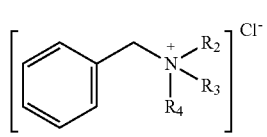

(II)

wherein R₂ and R₃ are independently selected from $C_{1-6}$ alkyl and R₄ is $C_{8-18}$ alkyl or —(CH₂CH₂O)₂[4-(1-dimethyl-3-dimethylbutyl)phenyl].

In particular embodiments, one or more of the following applies:
R₂ and R₃ are independently selected from methyl or ethyl, especially methyl; and
R₄ is selected from $C_8$, $C_{10}$, $C_{12}$, $C_{14}$, $C_{16}$ or $C_{18}$ alkyl or mixtures thereof or —(CH₂CH₂O)₂[4-(1-dimethyl-3-dimethylbutyl)phenyl].

The benzalkonium or benzethonium chloride compound is present in an amount in the range of about 0.1% to 1.0% w/w of the composition, especially about 0.1% to about 0.5% w/w, more especially about 0.1% to 0.2% w/w of the composition, and even more especially about 0.1% to 0.13% w/w of the composition in accordance with regulations according to the Federal Drug Administration 21 CFR Parts 333 and 369—Tentative Final Monograph for Health-Care Antiseptic Drug.

In some embodiments, the polymeric biguanide is a compound of formula (III):

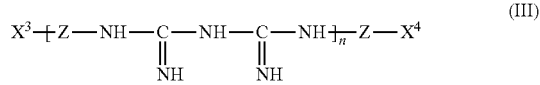

(III)

wherein Z is absent or an organic divalent bridging group and each Z may be the same or different throughout the polymer; n is at least 3, preferably 5 to 20 and X³ and X⁴ are independently selected from —NH₂, —NH—C(=NH)—NH—CN, optionally substituted alkyl, optionally substituted cycloalkyl, optionally substituted aryl, optionally substituted heterocyclyl and optionally substituted heteroaryl; or a pharmaceutically acceptable salt thereof. Preferably, the molecular weight of the polymeric compound is at least 1,000 amu, more preferably between 1,000 amu and 50,000 amu. In a single composition, n may vary providing a mixture of polymeric biguanides.

The above polymeric biguanide compounds and methods for their preparation are described in, for example, U.S. Pat. No. 3,428,576 and East et. al., 1997.

In some embodiments, the polymeric biguanide for use in the invention are polymeric alkylene biguanides of the following formula (IV):

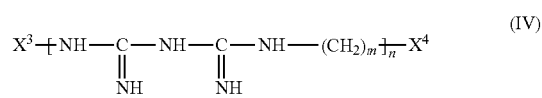

(IV)

wherein n is an integer from 3 to 500, m is an integer from 1 to 10, especially 3 (polyaminopropyl biguanide) or 6 (polyhexamethylene biguanide, PHMB) and X³ and X⁴ are independently selected from —NH₂, —NH—C(=NH)—NH—CN, optionally substituted alkyl, optionally substituted cycloalkyl, optionally substituted aryl, optionally substituted heterocyclyl and optionally substituted aryl or a pharmaceutically acceptable salt thereof. In particular embodiments, n has an average value of 3 to 15, more especially 3 to 12. A suitable polymeric biguanide is sold under the trade name Cosmocil CQ™ (Lonza), The polymeric biguanide is present in the composition in an amount in the range of 0.1% to 1.5% w/w, especially about 0.1% to about 1.0% w/w, more especially about 0.4% to about 0.6% w/w of the composition.

The surfactant system comprises an alcohol ethoxylate and an alkyl glucoside or alkylpolyglycoside.

In particular embodiments, the alcohol ethoxylate is a $C_{10-18}$ alcohol ethoxylate, especially a $C_{12-16}$ alcohol ethoxylate and more especially a $C_{12-15}$ alcohol ethoxylate group. In particular embodiments, the alcohol ethoxylate comprises 6 to 16 ethoxylate groups, especially about 10 to 14 ethoxylate groups. An example of a useful alcohol ethoxylate is $C_{12-15}$ Pareth-12™.

The alcohol ethoxylate is present in the composition in an amount in the range of 0.1% to 1.0% w/w, especially 0.2 to 0.8% w/w, more especially about 0.4 to 0.6% w/w of the composition.

In particular embodiments, the alkylglucoside or alkylpolyglycoside is a $C_{8-16}$ alkylglucoside or alkylpolyglycoside, or a mixture thereof. In some embodiments, the alkylglucoside or alkylpolyglycoside is selected from caprylyl glucoside, caprylyl/capryl glucoside, octyl glucoside, decyl glucoside, dodecyl glucoside, coco glucoside, lauryl glucoside, caprylyl polyglycoside, caprylyl/capryl polyglycoside, decyl polyglycoside, dodecyl polyglycoside, coco polyglycoside and lauryl polyglycoside.

The alkyl glucoside or alkylpolyglycoside is present in the composition in an amount in the range of 0.1% to 0.5% w/w, especially about 0.2 to 0.4% w/w of the composition.

In some embodiments, particularly those applications where the sanitizing composition is for application to skin, such as hands or feet, the composition may further comprise a moisturising, soothing, healing and antibacterial extract of aloe vera.

In some embodiments, the composition may also include other optional components such as rheological modifiers, pH adjustors, lubricants, humectants, fragrances and dyes. Suitable rheological modifiers include hydroxyethylcellulose, hydroxypropylcellulose and carbapol. Suitable pH adjustors include buffers, acids and bases. For example, a suitable acidic adjustor is acetic acid and a suitable basic adjustor is ammonium hydroxide. Other suitable acidic adjustors include sorbic acid and citric acid. Suitable lubricants or humectants include, for example, glycerin. Fragrances include essential oils and synthetic fragrances to provide the desirable odour. For example, a suitable fragrance is citronellol. Dyes or other colouring agents may also be included to impart a suitable colour to the composition. A suitable colouring agent is FD&C Blue No 1.i In some embodiments, the compositions are aqueous compositions wherein the carrier comprises water, especially where the carrier is water. In particular embodiments, the compositions of the invention do not include alcohol such as ethanol or methanol as a component.

The compositions may conveniently be in the form of a liquid, gel, cream, lacquer or foam. In some embodiments, the composition is impregnated in or coated on a textile to provide a wipe or swab. In some embodiments, the composition is dispersed from a dispenser, such as a pump action dispenser, that dispenses a predetermined amount of composition.

The gel formulations have a viscosity in the temperature range of 5° C. to 50° C. in the range of from 10,000 to 60,000 mPa·s, especially about 16,000 to 50,000 mPa·s. The lower the ambient temperature, the greater the viscosity. For example, at 25° C., the viscosity is in the range of from 31,000 to 32,000 mPa·s and at 50° C. the viscosity is in the range of from 16,000 to 17,000 mPa·s.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

As used herein, the term "alkyl" refers to a straight chain or branched saturated hydrocarbon group having 1 to 20 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl, decyl, isodecyl, undecyl, dodecyl and the like.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the term "alkylene" refers to a divalent saturated hydrocarbon chain having 1 to 6 carbon atoms. Where appropriate, the alkylene group may have a specified number of carbon atoms, for example, $C_{1-6}$alkylene includes alkylene groups having 1, 2, 3, 4, 5 or 6 carbon atoms in a linear arrangement. Examples of suitable alkylene groups include, but are not limited to, —$CH_2$—, —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—.

The term "heterocyclic" or "heterocyclyl" as used herein, refers to a cyclic hydrocarbon in which one to four carbon atoms have been replaced by heteroatoms independently selected from the group consisting of N, N(R), S, S(O), $S(O)_2$ and O. A heterocyclic ring may be saturated or unsaturated but not aromatic. A heterocyclic group may also be part of a spirocyclic group containing 1, 2 or 3 rings, two of which are in a "spiro" arrangement. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl and tetrazolyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

Alkyl, cycloalkyl, heterocyclyl, heteroaryl and aryl groups of the invention may be optionally substituted with 1 to 5 groups selected from OH, $OC_{1-6}$alkyl, Cl, Br, F, I, $NH_2$, $NH(C_{1-6}alkyl)$, $N(C_{1-6}alkyl)_2$, SH, $SC_{1-6}$alkyl, $CO_2H$, $CO_2C_{1-6}$alkyl, $CONH_2$, $CONH(C_{1-6}alkyl)$ or $CON(C_{1-6}alkyl)_2$.

As used herein, the term "divalent bridging group" refers to a radical that has a valence of two and is able to bind with two other groups. Examples of suitable divalent bridging groups include but are not limited to —$(CH_2)_t$— where t is an integer from 1 to 10, —O—, —S—, a divalent saturated or aromatic carbocyclic ring or a heterocyclic or heteroaromatic ring or a combination of such divalent and/or cyclic moieties. For example a saturated $C_6$ cyclic group would include —$C_6H_{10}$—, a $C_6$ aromatic group would include —$C_6H_4$—, a $C_6$ heterocyclic group would include

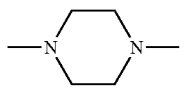

and a $C_6$ heteroaromatic would include

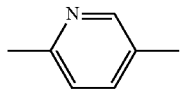

Other divalent bridging groups include alkylene groups (—$CH_2$—)$_t$ in which one or more carbon atoms have been replaced by NH, S, O,

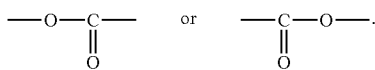

In a preferred embodiment the divalent bridging group is —$(CH_2)_t$— where t is an integer from 1 to 10, especially 1 to 6, more especially 3 to 6.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

The term "enclosed environment" refers to an indoor space or partial indoor space bound by at least one wall and a ceiling or roof. An enclosed environment may include partially outdoor areas such as covered balconies and covered decks.

Uses of the Sanitizing Compositions of the Invention

The sanitizing compositions of the present invention have antimicrobial activity that is useful in applications such as hand sanitation in hospitals, nursing homes, schools, child care facilities, and other places where there is a risk of the spread of microbial infection, especially antibiotic resistant microbial infection throughout a population, particularly patients in hospitals, the elderly in care and the young in child care or school.

The compositions of the present invention may readily be used as hand sanitizers to kill pathogens on the hands and avoid spreading of infection. The hand sanitizers may be applied to the hands in any suitable manner, for example, from a tube or pump action container or in the air stream of a hand drying device.

Without wishing to be bound by theory, it is thought that the composition forms a protective antimicrobial barrier on the skin. The compositions therefore not only provide control of microbes that are present when the composition is applied, they further protect the user from re-infection or infection upon exposure to further microbes they contact.

The sanitizing composition is effective against a wide range of pathogens which are either killed or inactivated following application of the composition. Pathogens which are killed or inactivated by the sanitizing compositions of the present invention include:

Gram Positive Bacteria

*Bacillus* sp. (vegetative cell), *Corynebacterium diptheriae, Clostridium difficile, Enterococcus faecalis, Enterococcus hirae, Listeria monocytogenes, Micrococcus luteus, Micrococcus* sp., *Mycobacterium tuberculosis, Mycobacterium smegmatis, Propionibacterium acnes, Staphylococcus aureus, Staphylococcus epidermidis, Staphylococcus haemolyticus, Staphylococus hominis, Staphylococcus saprophyticus, Streptococcus faecalis, Streptococcus mutans, Streptococcus pneumonia* and *Streptococcus pyogenes.*

Gram Negative Bacteria

*Acinetobacter baumannii, Acinetobacter calcoaceticus, Aeromonas hydrophilia, Bacterioides fragilis, Burkholderia cepacia Citrobacter deversus, Citrobacter freundi, Enterobacter aerogenes, Enterobacter aglomerans, Enterobacter cloacae, Enterobacter gergoviae, Enterococcus, Escherichia coli, Escherichia coli* O157:H7, *Eupenicillium levitum, Haemophilus influenza, Klebsiella oxytoca, Klebsiella pneumoniae, Klebsiella terriena, Legionella pneumophila, Morganella morganii, Penicillium luteum, Proteus mirabilis, Proteus vulgaris, Pseudomonas aeruginosa, Pseudomonas fluorscens, Salmonella cholera suis, Salmonella typhi, Salmonella typhimurium, Salmonella enterica, Serratia liquifaciens, Serratia marcescens* and *Xanthomonas campestris.*

Viruses

Adenovirus Type II & IV, Bovine Adenovirus Type I & IV, Murine Norovirus 1, Feline pneumonitis, Herpes Simplex Type I, Herpes Simplex Type II, HIV-1 (AIDS), Influenza A2 (Aichi), Influenza A2 (Asian), Influenza B, Influenza (H1N1), Mumps, Parinfluenza (Sendai), Rous Sarcoma, Reovirus Type I, Simian Virus 40, Vaccinia, MS2 (bacteriophage), PRD1 (bacteriophage), Rhinoviruses and Enterovirus 71.

Fungi, Algae, Mould, Yeast, Spores

*Alterania alternata, Aphanizomenon* sp., *Aspergillus flavus, Aspergillus niger, Aspergillus sydowii, Aspergillus terreus, Aspergillus versicolor, Aspergillus verrucaria, Aureobasidium pullans, Candida albicans, Candida pseudotropocalis, Chaetomium globsum, Cladosporium cladosporioides, Chlorella vulgaris, Dreschslera australiensis, Epidermophyton* sp., *Epidermophyton floccosum, Gliomastix cerealis, Gloeophyllum trabeum, Microsporum* sp., *Microsporum audouinii, Monilia grisea, Oscillatoria, Penicillium chrysogenum, Pencillium commune, Penicillium funiculosum, Penicillium pinophilum, Penicillium variable, Phoma fimeti, Pithomyces chartarum, Poria placenta, Scenedesmus, Saccharonyces cerevisiae, Scolecobasidium humicola, Selenastrum* sp., *Trichoderma viride, Trichophyton interdigitale, Trichophyton maidson, Trichophyton mentogrophytes, Trichophyton rubrum* and *Trichophyton* sp.

Protozoa Parasites

*Cryptosporidium Parvum* (Oocysts).

In light of their antifungal activity, the compositions of the present invention may also be useful in treating or preventing fungal infection of the skin, particularly those infections caused by *Tinea*, including Athlete's foot (*Tinea pedis*), *Tinea* of the scalp (*Tinea capitis*), *Tinea* of the hands (*Tinea manuum*), *Tinea* of the beard (*Tinea barbae*), jock itch (*Tinea cruris*) and *Tinea* of the body (*Tinea corporis*) or *Candida albicans* such as Intertrigo. In particular embodiments, the compositions useful in this method include aloe vera to assist in alleviating itching. In these embodiments, the composition is applied to the infected skin regularly, for example, multiple times per day, or once daily.

The compositions of the invention have been found to have not only immediate sanitizing effects on skin but also have been found to be persistent on the skin, providing a long-lasting protective effect. The protective effect can last for 3, 6 or 12 hours or more, or may last through a number of hand washing episodes or if hands are protected by surgical gloves. Immediate antimicrobial activity was demonstrated by a greater than 5.8 Log 10 reduction in bacterial flora immediately after use. Persistent activity is observed at the same order of magnitude 3 and 6 hours post treatment. Even 12 hours after treatment wherein the composition was applied to hands kept occluded within surgical gloves, only minimal lowering of antibacterial activity was observed (4 $\log_{10}$ reduction, 99.99%).

In yet another embodiment of the present invention, the compositions may be useful for sanitizing the air in an enclosed environment, such as a room or building. In these embodiments, the composition may be a liquid composition that is dispensed from a spray or aerosol dispenser. In some embodiments, the composition may be dispersed from a device by atomisation or formation of a fog or in an airstream. Suitable devices are described in WO 2013/149285. In particular embodiments, the building is a hospital. In some embodiments, the room is a ward of a hospital. In some embodiments, the sanitizing composition further comprises a fragrance to assist with deodorizing the air. Without wishing to be bound by theory, it is thought that negatively charged dust and bacterial particles in the air react with the positively charged aerosol droplets of composition of the invention. Agglomeration of particles occurs and the particles drop out of the air.

The invention will now be described with reference to the following Examples which illustrate some preferred aspects and embodiments of the present invention. However, it is to be understood that the particularity of the following description of the invention is not to supersede the generality of the preceding description of the invention.

EXAMPLES

Example 1: Antimicrobial Gel Formulation with Aloe Vera (Citronella Fragrance)

An antimicrobial formulation of a fragrant gel was made with the following components:

| | | |
|---|---|---|
| 1) | Water | 95.52% |
| 2) | Hydroxyethylcellulose | 1.55% |
| 3) | 1-Octadecanaminium-N,N-dimethyl-N-(3-trimethoxysilyl)propyl)chloride | 0.5% |
| 4) | $C_{12}$-$C_{15}$ Pareth-12 ™ | 0.50% |
| 5) | Polymeric biguanidine | 0.5% |
| 6) | Acetic acid | 0.3% |
| 7) | Caprylyl glucoside | 0.3% |
| 8) | DL citronellol | 0.3% |
| 9) | Ammonium hydroxide | 0.2% |
| 10) | Benzalkonium chloride | 0.13% |
| 11) | Glycerin | 0.10% |
| 12) | *Aloe* Extract | 0.05% |
| 13) | Blue No 1 | 0.0001% |

In Part A: Water was heated to 40° C. and the pH adjusted to pH 8. Hydroxethyl cellulose was added to the water and dissolved.

In Part B $C_{12}$-$C_{15}$ Pareth-12™, Caprylyl glucoside and Polymeric biguanidine as added to water preheated to 40° C. and the mixture was stirred.

The parts A and B were combined and the other ingredients were added maintaining the mixture at 40° C. The pH was adjusted to pH of 5.5 with acetic acid. The formulation was then cooled.

Example 2: Unscented Antimicrobial Gel Formulation with Aloe Vera

An antimicrobial formulation of an unscented gel was made with the following components:

| | | |
|---|---|---|
| 1) | Water | 95.82% |
| 2) | Hydroxyethylcellulose | 1.55% |
| 3) | 1-Octadecanaminium,N,N,dimethyl-N-(3-trimethoxysilyl) propyl) chloride | 0.5% |
| 4) | $C_{12}$-$C_{15}$ Pareth-12 ™ | 0.50% |
| 5) | Polymeric biguanidine | 0.5% |
| 6) | Acetic acid | 0.3% |
| 7) | Caprylyl glucoside | 0.3% |
| 8) | Ammonium hydroxide | 0.2% |
| 9) | Benzalkonium chloride | 0.13% |
| 10) | Glycerin | 0.10% |
| 11) | *Aloe* Extract | 0.05% |
| 12) | Blue No 1 | 0.0001% |

In Part A: Water was heated to 40° C. and the pH adjusted to pH 8. Hydroxethyl cellulose was added to the water and dissolved.

In Part B $C_{12}$-$C_{15}$ Pareth-12™, Caprylyl glucoside and Polymeric biguanidine as added to water preheated to 40° C. and the mixture was stirred.

The parts A and B were combined and the other ingredients were added maintaining the mixture at 40° C. The pH was adjusted to pH of 5.5 with acetic acid. The formulation was then cooled.

Example 3: Unscented Antimicrobial Liquid or Foam Formulation with Aloe Vera A formulation was prepared with the following components:

| | | |
|---|---|---|
| 1) | Water | 97.23% |
| 2) | 1-Octadecanaminium,N,N,dimethyl-N-(3-trimethoxysilyl) propyl) chloride | 1.0% |
| 3) | $C_{12}$-$C_{15}$ Pareth-12 ™ | 0.50% |
| 4) | Polymeric biguanidine | 1.0% |
| 5) | Sorbic acid | 0.1% |
| 6) | Caprylyl glucoside | 0.3% |
| 7) | Benzalkonium chloride | 0.13% |
| 8) | Glycerin | 0.10% |
| 9) | *Aloe* Extract | 0.05% |
| 10) | Blue No 1 | 0.001% |

The components are blended to form a liquid. Foam may be produced through a foam forming nozzle.

Example 4: Scented Antimicrobial Liquid or Foam Formulation with Aloe Vera (Citronella Fragrance)

A formulation was prepared from the following components:

| | | |
|---|---|---|
| 1) | Water | 97.23% |
| 2) | 1-Octadecanaminium,N,N,dimethyl-N-(3-trimethoxysilyl) propyl) chloride | 1.0% |
| 3) | $C_{12}$-$C_{15}$ Pareth-12 ™ | 0.50% |
| 4) | Polymeric biguanidine | 1.0% |
| 5) | Sorbic acid | 0.1% |
| 6) | Citronellol | 0.03 |
| 7) | Caprylyl glucoside | 0.3% |
| 8) | Benzalkonium chloride | 0.13% |
| 9) | Glycerin | 0.10% |
| 10) | *Aloe* Extract | 0.05% |
| 11) | Blue No 1 | 0.001% |

The components are blended to form a liquid. Foam may be produced through a foam forming nozzle.

Example 5: Antimicrobial Gel Formulation (Citronella Fragrance)

An antimicrobial formulation of a fragrant gel was made with the following components:

| | | |
|---|---|---|
| 1) | Water | 95.57% |
| 2) | Hydroxyethylcellulose | 1.55% |
| 3) | 1-Octadecanaminium-N,N-dimethyl-N-(3-trimethoxysilyl)propyl)chloride | 0.5% |
| 4) | $C_{12}$-$C_{15}$ Pareth-12 ™ | 0.50% |
| 5) | Polymeric biguanidine | 0.5% |
| 6) | Acetic acid | 0.3% |
| 7) | Caprylyl glucoside | 0.3% |
| 8) | DL citronellol | 0.3% |
| 9) | Ammonium hydroxide | 0.2% |
| 10) | Benzalkonium chloride | 0.13% |
| 11) | Glycerin | 0.10% |
| 12) | Blue No 1 | 0.0001% |

In Part A: Water was heated to 40° C. and the pH adjusted to pH 8. Hydroxethyl cellulose was added to the water and dissolved.

In Part B $C_{12}$-$C_{15}$ Pareth-12™, Caprylyl glucoside and Polymeric biguanidine as added to water preheated to 40° C. and the mixture was stirred.

The parts A and B were combined and the other ingredients were added maintaining the mixture at 40° C. The pH was adjusted to pH of 5.5 with acetic acid. The formulation was then cooled.

Example 6: Unscented Antimicrobial Gel Formulation

An antimicrobial formulation of an unscented gel was made with the following components:

| | | |
|---|---|---|
| 1) | Water | 95.87% |
| 2) | Hydroxyethylcellulose | 1.55% |
| 3) | 1-Octadecanaminium,N,N,dimethyl-N-(3-trimethoxysilyl) propyl) chloride | 0.5% |
| 4) | $C_{12}$-$C_{15}$ Pareth-12 ™ | 0.50% |
| 5) | Polymeric biguanidine | 0.5% |
| 6) | Acetic acid | 0.3% |
| 7) | Caprylyl glucoside | 0.3% |
| 8) | Ammonium hydroxide | 0.2% |
| 9) | Benzalkonium chloride | 0.13% |
| 10) | Glycerin | 0.10% |
| 11) | Blue No 1 | 0.0001% |

In Part A: Water was heated to 40° C. and the pH adjusted to pH 8. Hydroxethyl cellulose was added to the water and dissolved.

In Part B $C_{12}$-$C_{15}$ Pareth-12™, Caprylyl glucoside and Polymeric biguanidine as added to water preheated to 40° C. and the mixture was stirred.

The parts A and B were combined and the other ingredients were added maintaining the mixture at 40° C. The pH was adjusted to pH of 5.5 with acetic acid. The formulation was then cooled.

Example 7: Unscented Antimicrobial Liquid or Foam Formulation

A formulation was prepared with the following components:

| | | |
|---|---|---|
| 1) | Water | 97.28% |
| 2) | 1-Octadecanaminium,N,N,dimethyl-N-(3-trimethoxysilyl) propyl) chloride | 1.0% |
| 3) | $C_{12}$-$C_{15}$ Pareth-12 ™ | 0.50% |
| 4) | Polymeric biguanidine | 1.0% |
| 5) | Sorbic acid | 0.1% |
| 6) | Caprylyl glucoside | 0.3% |
| 7) | Benzalkonium chloride | 0.13% |
| 8) | Glycerin | 0.10% |
| 9) | Blue No 1 | 0.001% |

The components are blended to form a liquid. Foam may be produced through a foam forming nozzle.

Example 8: Scented Antimicrobial Liquid or Foam Formulation

A formulation was prepared from the following components:

| | | |
|---|---|---|
| 1) | Water | 97.28% |
| 2) | 1-Octadecanaminium,N,N,dimethyl-N-(3-trimethoxysilyl) propyl) chloride | 1.0% |
| 3) | $C_{12}$-$C_{15}$ Pareth-12 ™ | 0.50% |
| 4) | Polymeric biguanidine | 1.0% |
| 5) | Sorbic acid | 0.1% |
| 6) | Citronellol | 0.03 |

-continued

| | | |
|---|---|---|
| 7) Caprylyl glucoside | | 0.3% |
| 8) Benzalkonium chloride | | 0.13% |
| 9) Glycerin | | 0.10% |
| 10) Blue No 1 | | 0.001% |

The components are blended to form a liquid. Foam may be produced through a foam forming nozzle.

Example 9: Antimicrobial Efficacy of Formulations 2 and 3

The formulations of Examples 2 and 3 were subjected to the Time-Kill Assay for Antimicrobial Agents for 25 microbes in the Over the Counter (OTC) Antimicrobial Drug Monograph [FDA 1994, ASTM 2315, EN1276, EN1040 (bacteria) and EN1275 (fungi)]. The formulations of Examples 2 and 3 were compared to a 70% v/v ethanol hand sanitizer as a reference standard.

Briefly, in this method, a sample of each formulation was inoculated with a suspension of the test microorganism. After a series of pre-selected exposure times, a sample of the suspension is removed, neutralized and quantitatively assayed for surviving test microorganisms. After incubation, the surviving microorganisms were counted and the percent and $\log_{10}$ reductions determined at each time point against a control sample that did not contain formulation.

The results are shown in Table 1:

TABLE 1

Time-Kill Test Summary Showing Wide Spectrum & High Efficacy

| Micro-organism (Strain #) | Time (Sec) | 70% Alcohol Gel Hand Sanitizer | Hand Sanitizer Gel with Aloe Vera $\log_{10}$ reduction (%) | Hand Sanitizer Liquid/Foam with Aloe Vera $\log_{10}$ reduction (%) |
|---|---|---|---|---|
| Gram-Negative Bacteria | | | | |
| 1. *Acinetobacter baumannii* (ATCC #19606) | 15 sec | >6.04 (99.9999%) | >6.02 (99.9999%) | >6.02 (99.9999%) |
| | 30 sec | >6.04 (99.9999%) | >6.02 (99.9999%) | >6.02 (99.9999%) |
| | 60 sec | >6.04 (99.9999%) | >6.02 (99.9999%) | >6.02 (99.9999%) |
| 2. *Bacteroides fragilis* (ATCC# 25285) | 15 sec | >6.08 (99.9999%) | 6.03 (99.9999%) | 6.03 (99.9999%) |
| | 30 sec | >6.08 (99.9999%) | 6.03 (99.9999%) | 6.03 (99.9999%) |
| | 60 sec | >6.08 (99.9999%) | 6.03 (99.9999%) | 6.03 (99.9999%) |
| 3. *Haemophilus influenzae* (ATCC #33930) | 15 sec | >6.18 (99.9999%) | >6.12 (99.9999%) | >6.12 (99.9999%) |
| | 30 sec | >6.18 (99.9999%) | >6.12 (99.9999%) | >6.12 (99.9999%) |
| | 60 sec | >6.18 (99.9999%) | >6.12 (99.9999%) | >6.12 (99.9999%) |
| 4. *Enterobacter aerogenes* (ATCC #13048) | 15 sec | >6.08 (99.9999%) | >6.02 (99.9999%) | >6.02 (99.9999%) |
| | 30 sec | >6.08 (99.9999%) | >6.02 (99.9999%) | >6.02 (99.9999%) |
| | 60 sec | >6.08 (99.9999%) | >6.02 (99.9999%) | >6.02 (99.9999%) |
| 5. *Escherichia coli* (ATCC #11229) | 15 sec | >6.08 (99.9999%) | >6.01 (99.9999%) | >6.01 (99.9999%) |
| | 30 sec | >6.08 (99.9999%) | >6.01 (99.9999%) | >6.01 (99.9999%) |
| | 60 sec | >6.08 (99.9999%) | >6.01 (99.9999%) | >6.01 (99.9999%) |
| 6. *Escherichia coli* (ATCC #10536) | 15 sec | >6.08 (99.9999%) | >6.58 (99.9999%) | >6.78 (99.9999%) |
| | 30 sec | >6.08 (99.9999%) | >6.58 (99.9999%) | >6.78 (99.9999%) |
| | 60 sec | >6.08 (99.9999%) | >6.58 (99.9999%) | >6.78 (99.9999%) |
| 7. *Escherichia coli* (ATCC #25922) | 30 sec | >6.04 (99.9999%) | >5.0 (99.999%) | |
| | 60 sec | >6.04 (99.9999%) | >5.0 (99.999%) | |
| 8. *Klebsiella oxytoca* (ATCC #13182) | 15 sec | >6.04 (99.9999%) | >6.03 (99.9999%) | >6.03 (99.9999%) |
| | 30 sec | >6.08 (99.9999%) | >6.03 (99.9999%) | >6.03 (99.9999%) |
| | 60 sec | >6.08 (99.9999%) | >6.03 (99.9999%) | >6.03 (99.9999%) |
| 9. *Escherichia coli* (O157:H7) | 15 sec | >6.08 (99.9999%) | >4.0 (>99.99%) | |
| 10. *Klebsiella pneumoniae* (ATCC #51504) | 15 sec | >6.18 (99.9999%) | >5.0 (99.999%) | |
| | 30 sec | >6.18 (99.9999%) | >5.0 (99.999%) | |
| | 60 sec | >6.18 (99.9999%) | >5.0 (99.999%) | |
| 11. *Klebsiella pneumoniae* (ATCC #4352) | 15 sec | >6.08 (99.9999%) | >6.04 (99.9999%) | >6.04 (99.9999%) |
| | 30 sec | >6.08 (99.9999%) | >6.04 (99.9999%) | >6.04 (99.9999%) |
| | 60 sec | >6.08 (99.9999%) | >6.04 (99.9999%) | >6.04 (99.9999%) |
| 12. *Pseudomonas aeruginosa* (ATCC #9027) | 15 sec | >6.08 (99.9999%) | >6.58 (99.9999%) | >6.78 (99.9999%) |
| | 30 sec | >6.08 (99.9999%) | >6.58 (99.9999%) | >6.78 (99.9999%) |
| | 60 sec | >6.08 (99.9999%) | >6.58 (99.9999%) | >6.78 (99.9999%) |
| 13. *Pseudomonas aeruginosa* (ATCC #27853) | 15 sec | >6.08 (99.9999%) | >6.23 (99.9999%) | >6.23 (99.9999%) |
| | 30 sec | >6.08 (99.9999%) | >6.23 (99.9999%) | >6.23 (99.9999%) |
| | 60 sec | >6.08 (99.9999%) | >6.23 (99.9999%) | >6.23 (99.9999%) |
| 14. *Pseudomonas aeruginosa* (ATCC #27853) | 15 sec | | >5.0 (99.999%) | |
| | 30 sec | | >5.0 (99.999%) | |
| | 60 sec | | >5.0 (99.999%) | |

TABLE 1-continued

Time-Kill Test Summary Showing Wide Spectrum & High Efficacy

| Micro-organism (Strain #) | Time (Sec) | 70% Alcohol Gel Hand Sanitizer | Hand Sanitizer Gel with *Aloe Vera* Log$_{10}$ reduction (%) | Hand Sanitizer Liquid/Foam with *Aloe Vera* Log$_{10}$ reduction (%) |
|---|---|---|---|---|
| 15. *Pseudomonas aeruginosa* (ATCC #15442) | 15 sec | | >5.0 (99.999%) | |
| | 30 sec | | >5.0 (99.999%) | |
| | 60 sec | | >5.0 (99.999%) | |
| 16. *Proteus mirabilis* (ATCC #7002) | 15 sec | >6.01 (99.9999%) | >6.12 (99.9999%) | >6.12 (99.9999%) |
| | 30 sec | >6.01 (99.9999%) | >6.12 (99.9999%) | >6.12 (99.9999%) |
| | 60 sec | >6.01 (99.9999%) | >6.12 (99.9999%) | >6.12 (99.9999%) |
| 17. *Serratia marcescens* (ATCC #14756) | 15 sec | >6.03 (99.9999%) | >6.12 (99.9999%) | >6.12 (99.9999%) |
| | 30 sec | >6.03 (99.9999%) | >6.12 (99.9999%) | >6.12 (99.9999%) |
| | 60 sec | >6.03 (99.9999%) | >6.12 (99.9999%) | >6.12 (99.9999%) |
| 18. *Salmonella enterica* GFS- (ATCC #10398) | 60 sec | | >5.0 (99.999%) | |
| 19. *Salmonella typhimurium*[1] | 15 sec | | >4.0 (99.99%) | |

Gram-Positive Bacteria

| Micro-organism (Strain #) | Time (Sec) | 70% Alcohol Gel Hand Sanitizer | Hand Sanitizer Gel with *Aloe Vera* Log$_{10}$ reduction (%) | Hand Sanitizer Liquid/Foam with *Aloe Vera* Log$_{10}$ reduction (%) |
|---|---|---|---|---|
| 20. *Staphylococcus aureus* (ATCC #6538) | 15 sec | >6.06 (99.9999%) | >6.56 (99.9999%) | 6.76 (99.9999%) |
| | 30 sec | >6.06 (99.9999%) | >6.56 (99.9999%) | 6.76 (99.9999%) |
| | 60 sec | >6.06 (99.9999%) | >6.56 (99.9999%) | 6.76 (99.9999%) |
| 21. *Staphylococcus aureus* (ATCC #29213) | 15 sec | >6.08 (99.9999%) | >6.11 (99.9999%) | >6.11 (99.9999%) |
| | 30 sec | >6.08 (99.9999%) | >6.11 (99.9999%) | >6.11 (99.9999%) |
| | 60 sec | >6.08 (99.9999%) | >6.11 (99.9999%) | >6.11 (99.9999%) |
| 22. *Staphylococcus epidermidis* (ATCC #12228) | 15 sec | >6.28 (99.9999%) | >6.22 (99.9999%) | >6.22 (99.9999%) |
| | 30 sec | >6.28 (99.9999%) | >6.22 (99.9999%) | >6.22 (99.9999%) |
| | 60 sec | >6.28 (99.9999%) | >6.22 (99.9999%) | >6.22 (99.9999%) |
| 23. *Staphylococcus hominis* (ATCC #27844) | 15 sec | >6.22 (99.9999%) | >6.21 (99.9999%) | >6.21 (99.9999%) |
| | 30 sec | >6.22 (99.9999%) | >6.21 (99.9999%) | >6.21 (99.9999%) |
| | 60 sec | >6.22 (99.9999%) | >6.21 (99.9999%) | >6.21 (99.9999%) |
| 24. *Staphylococcus haemolyticus* (ATCC #43253) | 15 sec | | >5.0 (99.999%) | |
| | 30 sec | | >5.0 (99.999%) | |
| | 60 sec | | >5.0 (99.999%) | |
| 25. *Staphylococcus haemolyticus* (ATCC #29970) | 15 sec | >6.16 (99.9999%) | >6.12 (99.9999%) | >6.12 (99.9999%) |
| | 30 sec | >6.16 (99.9999%) | >6.12 (99.9999%) | >6.12 (99.9999%) |
| | 60 sec | >6.16 (99.9999%) | >6.12 (99.9999%) | >6.12 (99.9999%) |
| 26. *Staphylococcus saprophyticus* (ATCC #35552) | 15 sec | >6.16 (99.9999%) | >6.11 (99.9999%) | >6.11 (99.9999%) |
| | 30 sec | >6.16 (99.9999%) | >6.11 (99.9999%) | >6.11 (99.9999%) |
| | 60 sec | >6.16 (99.9999%) | >6.11 (99.9999%) | >6.11 (99.9999%) |
| 27. *Micrococcus luteus* (ATCC #7468) | 15 sec | >6.26 (99.9999%) | >6.22 (99.9999%) | >6.22 (99.9999%) |
| | 30 sec | >6.26 (99.9999%) | >6.22 (99.9999%) | >6.22 (99.9999%) |
| | 60 sec | >6.26 (99.9999%) | >6.22 (99.9999%) | >6.22 (99.9999%) |
| 28. *Streptococcus pyogenes* (ATCC #19615) | 15 sec | >6.08 (99.9999%) | >6.03 (99.9999%) | >6.03 (99.9999%) |
| | 30 sec | >6.08 (99.9999%) | >6.03 (99.9999%) | >6.03 (99.9999%) |
| | 60 sec | >6.08 (99.9999%) | >6.03 (99.9999%) | >6.03 (99.9999%) |
| 29. *Enterococcus faecalis* (ATCC# 29212) | 15 sec | >6.08 (99.9999%) | >6.01 (99.9999%) | >6.01 (99.9999%) |
| | 30 sec | >6.08 (99.9999%) | >6.01 (99.9999%) | >6.01 (99.9999%) |
| | 60 sec | >6.08 (99.9999%) | >6.01 (99.9999%) | >6.01 (99.9999%) |
| 30. *Enterococcus hirae* (ATCC #6057) | 15 sec | >6.06 (99.9999%) | >6.56 (99.9999%) | >6.76 (99.9999%) |
| | 30 sec | >6.06 (99.9999%) | >6.56 (99.9999%) | >6.76 (99.9999%) |
| | 60 sec | >6.06 (99.9999%) | >6.56 (99.9999%) | >6.76 (99.9999%) |
| 31. *Streptococcus pneumoniae* (ATCC #8043) | 15 sec | >6.08 (99.9999%) | >6.06 (99.9999%) | >6.06 (99.9999%) |
| | 30 sec | >6.08 (99.9999%) | >6.06 (99.9999%) | >6.06 (99.9999%) |
| | 60 sec | >6.08 (99.9999%) | >6.06 (99.9999%) | >6.06 (99.9999%) |

Fungi (Yeast & Mold)

| Micro-organism (Strain #) | Time (Sec) | 70% Alcohol Gel Hand Sanitizer | Hand Sanitizer Gel with *Aloe Vera* Log$_{10}$ reduction (%) | Hand Sanitizer Liquid/Foam with *Aloe Vera* Log$_{10}$ reduction (%) |
|---|---|---|---|---|
| 32. *Candida albicans* (ATCC# 10231) | 15 sec | >5.42 (99.9995%) | >5.22 (99.999%) | >5.12 (99.9999%) |
| | 30 sec | >5.42 (99.9995%) | >5.22 (99.999%) | >5.12 (99.9999%) |
| | 60 sec | >5.42 (99.9995%) | >5.22 (99.999%) | >5.12 (99.9999%) |
| 33. *Aspergillus niger* (ATCC# 16404) | 15 sec | >5.54 (99.9996%) | >5.04 (99.999%) | >5.44 (99.9995%) |
| | 30 sec | >5.54 (99.9996%) | >5.04 (99.999%) | >5.44 (99.9995%) |
| | 60 sec | >5.54 (99.9996%) | >5.04 (99.999%) | >5.44 (99.9995%) |

Example 10: Viral Efficacy of Sanitizer Composition

The sanitizer formulation of Example 6 was tested for efficacy against Norwalk Virus, on fresh, washed, shaved and sterilized porcine skin to simulate human skin contact. The virus stock is prepared using the following materials. Norwalk Virus (MNV-1) animal CW1, ATCC PTA-5935 hosted in RAW 264.7 Murine cells, ATCC T1B71. Once confluency is obtained, the stock was tested on a set of porcine skin, M121015D, pads (3"×6" pads) without the sanitizer (control) to ensure this can be used as a suitable substrate for challenging the product. On all three sets of pig skin pads, the Norwalk virus is applied, dried and treated with sanitizer composition. The pads are sampled and evaluated for viability of Norwalk virus. The second and third sets of pads were repeatedly washed with a mild non-antimicrobial soap to simulate hand-washing. The second set of pads were washed five times and the third set of pads washed nine times. Each set of pads were sampled to evaluate viability of Norwalk virus. Following the five and nine washings, each set of pads were contaminated again with Norwalk virus, dried and sampled to determine long-term protection of the initial application of the product. An additional control was added to ensure no interference from the mild antimicrobial soap washings of the porcine skin pads on the procedure.

The results are shown in Table 2.

TABLE 2

| Sample ID | Description | Application | Results | Comments |
| --- | --- | --- | --- | --- |
| Control | Virus applied and dried on porcine skin followed by rinsing | None | 100% infected | Plaque assay performed. Viability confirmed following 72 hours of incubation |
| Control | Porcine pads were washed 9 times followed by contamination with virus stock | Mild antimicrobial salt | 100% infected | Plaque assay performed. Viability confirmed following 72 hours of incubation |
| Product applied | Product applied to porcine pads and rubbed to dryness | Composition of Example 6 applied; No soap washing | Dead | Cells are infected and dead |
| Product applied | Product applied to porcine pads and rubbed to dryness | Composition of Example 6 applied | Dead | Cells are infected and dead |
| Product applied 5 x washing | Product applied to porcine pads and rubbed to dryness; washed 5 x | Composition of Example 6 applied. Mild antimicrobial soap | Dead | Cells are infected and dead |
| Product applied 5 x washing Recontamination with stock virus | Product applied to porcine pads and rubbed to dryness; washed 5 x. Virus reapplied and dried followed by rinsing after 5 min | Composition of Example 6 applied. Mild antimicrobial soap | 50-60% infected | Some viability indicating some level of protection following five washings |
| Product applied | Product applied to porcine pads and rubbed to dryness | Composition of Example 6 applied | Dead | Cells infected and dead |
| Product applied | Product applied to porcine pads and rubbed to dryness; washed 5 x. | Composition of Example 6 applied. Mild antimicrobial soap | Dead | Cells are infected and dead |
| Product applied 9 x washing Recontamination with stock virus | Product applied to porcine pads and rubbed to dryness; washed 5 x. Virus reapplied and dried followed by rinsing after 5 min | Composition of Example 6 applied. Mild antimicrobial soap | 100% infected | Viability indicating no level of protection following nine washings |

Example 11: Antibacterial Efficacy

The experiment was executed to evaluate the effectiveness of the sanitizer product of Example 6 for a Time-Kill Assay using the procedure outlined I ASTM method E2315-03 on the following species and strains: *Escherichia coli* (ATCC 11229), *Salmonella enterica* (ATCC 10306), *Staphylococcus aureus* (ATCC 6538), *Streptococcus pyogenes* (ATCC 19615) and *Pseudomonas aeruginosa* (ATCC 15442). Each organism was checked and evaluated independent of one another to ensure direct effects on the organism by the formulation and to eliminate any effects of one bacterium on another. All media preparation was specific to each organism. Samples were drawn and plated in duplicate. The results are reported as the mean of the duplicate samples. All testing was conducted at ambient temperature. *Streptococcus* pyrogenes was incubated in a 5% carbon dioxide environment for successful growth. The microorganisms were challenged with the letheen broth used for neutralizing the sanitizer composition, to ensure it did not have any problematic effects on the growth of the organism.

The results are shown in Table 3.

TABLE 3

| Organism | Time in seconds Control | Results (CFUs) Growth | Comments Conditions and media support growth |
| --- | --- | --- | --- |
| *Escherichia coli* | 0 | 0 | No growth was observed at any time |
|  | 15 | 0 |  |
|  | 30 | 0 |  |
|  | 60 | 0 |  |
| *Salmonella enterica* | 0 | 5 | The organism showed some ability to resist the effects of the sanitizer but succumbed at 60 seconds |
|  | 15 | 2 |  |
|  | 30 | 1 |  |
|  | 60 | 0 |  |
| *Staphylococcus aureus* | 0 | 0 | No growth was observed at any time |
|  | 15 | 0 |  |
|  | 30 | 0 |  |
|  | 60 | 0 |  |
| *Streptococcus pyogenes* | 0 | 7 | The organism showed some ability to resist the effects of the sanitizer but succumbed at 60 seconds |
|  | 15 | 4 |  |
|  | 30 | 1 |  |
|  | 60 | 0 |  |
| *Pseudomonas aeruginosa* | 0 | 0 | No growth was observed at any time |
|  | 15 | 0 |  |
|  | 30 | 0 |  |
|  | 60 | 0 |  |

Example 12: Antibacterial Efficacy

The experiment was executed to evaluate the effectiveness of the sanitizer product of Example 2 for a Time-Kill Assay using the procedure outlined I ASTM method E2315-03 on the following species and strains: *Escherichia coli* (ATCC 11229), *Salmonella enterica* (ATCC 10306) *Staphylococcus aureus* (ATCC 6538), *Streptococcus pyrogenes* (ATCC 19615) and *Pseudomonas aeruginosa* (ATCC 15442). Each organism was checked and evaluated independent of one another to ensure direct effects on the organism by the formulation and to eliminate any effects of one bacterium on another. All media preparation was specific to each organism. Samples were drawn and plated in duplicate. The results are reported as the mean of the duplicate samples. All testing was conducted at ambient temperature. *Streptococcus pyrogenes* was incubated in a 5% carbon dioxide environment for successful growth. The microorganisms were challenged with the letheen broth used for neutralizing the sanitizer composition, to ensure it did not have any problematic effects on the growth of the organism.

The results are shown in Table 4.

TABLE 4

| Organism | Time in seconds Control | Results (CFUs) Growth | Comments Conditions and media support growth |
| --- | --- | --- | --- |
| Escherichia coli | 0 | 0 | No growth was observed at any time |
|  | 15 | 0 |  |
|  | 30 | 0 |  |
|  | 60 | 0 |  |
| Salmonella enterica | 0 | 5 | The organism showed some ability to resist the effects of the sanitizer but succumbed at 60 seconds |
|  | 15 | 2 |  |
|  | 30 | 1 |  |
|  | 60 | 0 |  |
| Staphylococcus aureus | 0 | 0 | No growth was observed at any time |
|  | 15 | 0 |  |
|  | 30 | 0 |  |
|  | 60 | 0 |  |
| Streptococcus pyrogenes | 0 | 7 | The organism showed some ability to resist the effects of the sanitizer but succumbed at 60 seconds |
|  | 15 | 4 |  |
|  | 30 | 1 |  |
|  | 60 | 0 |  |
| Pseudomonas aeruginosa | 0 | 0 | No growth was observed at any time |
|  | 15 | 0 |  |
|  | 30 | 0 |  |
|  | 60 | 0 |  |

Example 13: Antibacterial Efficacy

The experiment was executed to evaluate the effectiveness of the sanitizer product of Example 2 for a Time-Kill Assay using the procedure outlined in ASTM method E2315-03 on the following species and strains: *Escherichia coli* (ATCC 25922), *Klebsiella pneumoniae* (ATCC 51504), *Pseudomonas aeruginosa* (ATCC 27853), *Staphylococcus aureus* (ATCC 29213) and *Staphylococcus haemolyticus* (ATCC 43253). Each organism was checked and evaluated independent of one another to ensure direct effects on the organism by the formulation and to eliminate any effects of one bacterium on another. All media preparation was specific to each organism. Samples were drawn and plated in duplicate. The results are reported as the mean of the duplicate samples. All testing was conducted at ambient temperature.

The results are shown in Table 5.

TABLE 5

| Organism | Time in seconds Control | Results (CFUs) Growth | Comments Conditions and media support growth |
| --- | --- | --- | --- |
| Escherichia coli | 0 | 2 | Some viability but succumbed by 15 seconds |
|  | 15 | 0 |  |
|  | 30 | 0 |  |
|  | 60 | 0 |  |
| Klebsiella pneumoniae | 0 | 0 | No growth was observed at any time |
|  | 15 | 0 |  |
|  | 30 | 0 |  |
|  | 60 | 0 |  |
| Pseudomonas aeruginosa | 0 | 0 | No growth was observed at any time |
|  | 15 | 0 |  |
|  | 30 | 0 |  |
|  | 60 | 0 |  |
| Staphylococcus aureus | 0 | 0 | No growth was observed at any time |
|  | 15 | 0 |  |
|  | 30 | 0 |  |
|  | 60 | 0 |  |
| Staphylococcus haemolyticus | 0 | 0 | No growth was observed at any time |
|  | 15 | 0 |  |
|  | 30 | 0 |  |
|  | 60 | 0 |  |

Example 14: Persistent Antibacterial Efficacy

Samples of porcine skin were cut into pads measuring about 3×6 inches and sterilized with 70% ethanol (2 mL). A test group were treated with a composition of Example 2 and left at room temperature for up to four hours. At predetermined intervals, inocula of MRSA (ATCC #33592), VRE (ATCC #51575) and CRE (*Klebsiella pneumoniae*, ATCC # BAA-1705). The pads were washed and treated to obtain any living bacteria and samples were plated, incubated and counted to determine live bacteria. The samples were compared to samples treated in the same manner but without skin sanitizer. Inoculations were made at 2 minutes, 1 hour and 5 hours after application of the sanitizer composition.

All samples at each timepoint had 99.9999% (>5.8 $\log_{10}$ reduction) bacterial growth reduction compared to those samples that had not been treated with sanitizer composition.

Example 15: Persistent Antibacterial Efficacy

The protocol for Example 14 was repeated with *Staphylococcus aureus* (ATCC #12600) with inoculation times of 2 minutes, 1 hour, 2 hours, 4 hours, 8 hours, 16 hours and 24 hours.

The results show an initial 3 $\log_{10}$ reduction in bacterial growth, followed by 99% suppression at 1 hour, 98% suppression at 2 hours, 97% suppression at 4 hours, 85% suppression at 8 hours, 80% suppression at 16 hours and 54% suppression at 24 hours.

Example 16: Efficacy of Example 2 as a Handrub

The composition of Example 2 was tested for compliance with requirements for chemical disinfectants and antiseptics in accordance with European Standard BS EN 1500:2013 Chemical Disinfectants and Antiseptics—Hygienic Handrub—Test Method and Requirements. The test organism was *Escherichia coli* K12 NCTC 10538 which was obtained as a freeze dried ampoule and was reconstituted using Tryptone Soy Broth and incubated to achieve a concentration of 2×10⁹ Cfu/mL. The reference standard was propan-2-ol 60% v/v solution in sterile water. There were no deviations from the standard test method.

Human volunteer's hands were washed for 1 minute with diluted soft soap (5 mL), rinsed in running water and dried with a paper towel for at least 30 seconds. The hands were immersed up to the mid-metacarpals for five seconds and the liquid was allowed to drain back into the container for a maximum of 30 seconds before allowing to air dry for three minutes.

The reference standard (3.0 mL) was applied and rubbed for 30 seconds. This was repeated with a second portion of reference standard (3.0 mL) and rubbing for a further 30 seconds. This procedure was repeated for 20 volunteers.

This protocol was repeated on 20 volunteers using the composition of Example 2.

Analysis of the results showed that the reference standard had a Mean Log Reduction Factor of 3.89 and the composition of Example 2 had a Mean Log Reduction Factor of 4.22. The Mean Log Reduction Factor of the test product was greater than that of the reference standard, therefore the composition of Example 2 is more effective than the propan-2-ol standard reference and passes the requirements for EN 1500 for hygienic handrubs.

Example 17: Efficacy of Example 4 as a Handrub

The protocol of Example 16 was repeated for the composition of Example 4.

Analysis of the results showed that the reference standard had a Mean Log Reduction Factor of 3.90 and the composition of Example 2 had a Mean Log Reduction Factor of 4.23. The Mean Log Reduction Factor of the test product was greater than that of the reference standard, therefore the composition of Example 4 is more effective than the reference and passes the requirements for EN 1500 for hygienic handrubs.

Example 18: Virucidal Quantitative Suspension Test

The composition of Example 2 was tested to evaluate its virus-inactivating properties using the Virucidal Quantitative Suspension Test for Chemical Disinfectants and Antiseptics in accordance with European Standard BS EN 14476:2005 Chemical Disinfectants and Antiseptics used in Human Medicine (British Standards Institution, 389 Chiswick High Road, London).

The virucidal studies were carried out at 80% concentration using contact times of 1, 5, 15, 30 and 60 minutes using Rhinovirus (common cold; ATCC VR-482), Influenza virus (ATCC VR-1741) and Enterovirus 71 (hand, foot and mouth disease virus; ATCC VR-1775) as test viruses.

The test virus suspension was prepared according to test standard clause 6.3. BGM cells were cultivated with Dulbecco's Modified Eagles Medium and 10% fetal calf serum. Rhinovirus (common cold), Influenza virus and Enterovirus 71 (hand, foot and mouth disease virus) were added to the monolayer for 1 hour at 37° C. Cells were subjected to a threefold freeze/thaw process. Cellular debris was removed by low speed centrifugation and the supernatant was stored at −80° C. as test virus suspension.

Infectivity was determined from the endpoint according to test standard clause 6.5.1. 0.1 mL of each dilution was transferred into eight wells of a 96-well microtitre plate, followed by addition of 0.1 mL of freshly trypsinised BGM cells. Microtitre plates were incubated at 37° C. in a 5% $CO_2$ atmosphere. The cytopathic effect was determined after 7 days using an inverted microscope. The estimated virus concentration was calculated using the Spearman-Kärber method (BS EN 14476 clause 1.1).

Determination of virucidal activity was determined according to test standard clause 6.6. The sample was examined as an 80% solution in hard water (clause 5.2.2.2). Contact times were 1, 5, 15, 30 and 60 minutes. The volume of test virus suspension was 0.1 mL, interfering substance (0.1 mL) and test product (0.8 mL). Activity of the disinfectant was stopped by dilution to $10^{-8}$ immediately at the end of the desired contact time. Titration of the virus control was performed at contact times of 0 minutes and 60 minutes (clause 6.6.8).

Determination of cytotoxicity was performed according to test standard clause 6.6.4.1 with hard water (200 µL) and test product (800 µL). Cell sensitivity to virus was determined by comparative virus titration on cells in the presence and absence of disinfectant (clause 6.6.4.2 b). Formaldehyde solution (0.7%) was used as a reference standard (clause 6.6.7.1). Cytotoxicity of the formaldehyde solution was determined according to test standard clause 6.6.7.2 with dilutions up to $10^{-5}$. Contact times were 5, 15, 30 and 60 minutes.

The composition of Example 2 demonstrated effectiveness as an 80% solution against Rhinovirus, Influenza virus and Enterovirus 71 after a contact time of 60 minutes. The reduction exceeded 4 $\log_{10}$-steps. It is concluded that the composition of Example 2 is virucidal against Rhinovirus (common cold), Influenza virus and Enterovirus 71 (hand, foot and mouth disease virus)

Example 19: Virucidal Quantitative Suspension Test

The protocol of Example 18 was repeated for the composition of Example 4 to evaluate its virus-inactivating properties.

The composition of Example 4 was shown to inactivate Rhinovirus, Influenza virus and Enterovirus 71 after a contact time of 60 minutes. The reduction exceeded 4 $\log_{10}$-steps. It is concluded that the composition of Example 4 is virucidal against Rhinovirus (common cold), Influenza virus and Enterovirus 71 (hand, foot and mouth disease virus).

Example 20: Activity, Persistent Activity and Cumulative Activity

The composition of Example 2 was tested to evaluate the activity of the test formulation in reducing the bacterial population of the hands immediately after a single use and to determine persistent activity (inhibition of growth) after three hours and six hours. Cumulative activity measurements were made over a five day period. The composition was tested in accordance with the protocol of ASTM E115-11—Standard Test Method for Evaluation of Surgical Hand Scrub Formulations (ASTM International, 100 Barr Harbor Drive, West Conshohocken, Pa., USA).

The immediate activity ($\log_{10}$ reduction) was calculated from the average baseline $\log_{10}$ of a volunteer's hand minus the $\log_{10}$ of the post-treatment count for that hand. The composition of Example 2 showed 100% bacterial reduction after using this composition. Persistent activity was calculated from the variance in $\log_{10}$ reduction after 3, 6 and 12 hours glove wear. Results showed that bacterial reduction was 100% after three hours ($\sigma^2_{3h}=0$) and six hours ($\sigma^2_{6h}=0$). The bacterial reduction after 12 hours was a minimum of 99.5% ($\sigma^2_{12h}=6.25\times10^{-6}$).

Cumulative activity results for Day 1 (two applications of composition) and Day 5 (12 applications of composition) both showed 100% bacterial reduction. In conclusion, the composition of Example 2 had an obvious sterilisation effect.

Example 21: Activity, Persistent Activity and Cumulative Activity

The composition of Example 4 was tested in accordance with the protocol of Example 20.

When tested in accordance with ASTM E1115-11, the composition of Example 4 showed 100% bacterial reduction after using the formulation. Persistent activity results showed that bacterial reduction was 100% after three hours and six hours. The bacterial reduction after 12 hours was a minimum of 99.5%. Cumulative activity results showed that Day 1 (two applications of composition) and Day 5 (12 applications of composition) both demonstrated 100% bacterial reduction. In conclusion, the composition of Example 4 had an obvious sterilisation effect.

The claims defining the invention are as follows:

1. A sanitizing composition comprising:
   i) 0.1% to 1.5% w/w of an alkoxy silyl ammonium film-forming compound;
   ii) 0.1% to 1.0% w/w of a benzalkonium or benzethonium chloride;
   iii) 0.1% to 1.5% w/w of a polymeric biguanide;
   iv) a surfactant system comprising:
      a. 0.1% to 1% w/w of an alcohol ethoxylate; and
      b. 0.1% to 0.5% w/w of an alkylglucoside or alkylpolyglycoside; and
   v) an aqueous carrier;
wherein said composition comprises no ethyl alcohol;
wherein said composition is effective in sanitizing human skin surface;
wherein said composition provides >$10^6$/mL reduction of *Staphylococcus aureus* (ATCC 6538) within 60 seconds as measured under ASTM 2315-03;
wherein the pH of the composition is about 5.5; and
wherein the composition comprises glycerin.

2. The sanitizing composition according to claim 1 wherein the alkoxy silyl ammonium film-forming compound is selected from 3-trimethoxysilylpropyl-N,N-dimethyl-N-octadecyl ammonium chloride, 3-triethoxysilylpropyl-N,N-dimethyl-N-octadecyl ammonium chloride, 3-triethoxysilylpropyl-N,N-dimethyl-N-isodecyl ammonium chloride and 3-trimethoxysilylpropyl-N,N-dimethyl-N-isodecyl ammonium chloride.

3. The sanitizing composition according to claim 1 wherein the polymeric biguanide is a polyaminopropyl biguanide or polyhexamethylene biguanide.

4. The sanitizing composition according to claim 1 wherein the polymeric biguanide is present in an amount of 0.1% to 1.0% w/w of the composition.

5. The sanitizing composition according to claim 1 wherein the alcohol ethoxylate surfactant is a C12-18 alcohol ethoxylate comprising 6 to 16 moles of ethylene oxide.

6. The sanitizing composition according to claim 1 wherein the alkylglucoside surfactant is caprylyl glucoside.

7. The sanitizing composition according to claim 1 further comprising a dye or an extract of aloe vera.

8. The sanitizing composition of claim 1, wherein said composition provides a persistent antibacterial efficacy to porcine skin pads against methicillin-resistant *Staphylococcus aureus* (MRSA) strain ATCC 33592 at 5 hours after the composition is applied to the skin pads; said persistent antibacterial efficacy providing greater than a 5.8 $\log_{10}$ reduction in methicillin-resistant bacterial growth compared to porcine skin pads treated in the same manner without application of the sanitizer composition.

9. The sanitizing composition according to claim 1 in the form of a liquid.

10. The sanitizing composition according to claim 1 in the form of a gel.

11. A method of sanitizing or disinfecting skin comprising applying to the skin, the sanitizing composition of claim 1.

12. A method according to claim 11 wherein the skin is the skin of hands or feet.

13. A method of treating a fungal infection of the skin, comprising applying the sanitizing composition according to claim 1 to the skin of a subject.

14. A method according to claim 13 wherein the fungal infection is a *Tinea* infection.

* * * * *

UNITED STATES PATENT AND TRADEMARK OFFICE
CERTIFICATE OF CORRECTION

Page 1 of 1

PATENT NO. : 11,051,516 B2
APPLICATION NO. : 15/126855
DATED : July 6, 2021
INVENTOR(S) : Paul Geoffrey Smyth et al.

It is certified that error appears in the above-identified patent and that said Letters Patent is hereby corrected as shown below:

On the Title Page

In Item (71), under "Applicant", in Column 1, delete "GFS CORPORATION AUS PTY LTD, Narangba (AU)" and insert --GLOBAL BIOPROTECT IP PTY LTD, Willoughby (AU)--, therefor.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*